United States Patent
Kimura et al.

(10) Patent No.: US 9,902,747 B2
(45) Date of Patent: Feb. 27, 2018

(54) PHOSPHITE COMPOUND, METHOD FOR PRODUCING THE SAME AND USES THEREOF

(71) Applicant: SUMITOMO CHEMICAL COMPANY, LIMITED, Tokyo (JP)

(72) Inventors: Natsuko Kimura, Osaka (JP); Orhan Ozturk, Tokyo (JP); Kazumasa Matsuo, Osaka (JP)

(73) Assignee: SUMITOMO CHEMICAL COMPANY, LIMITED, Chuo-ku, Tokyo (JP)

( * ) Notice: Subject to any disclaimer, the term of this patent is extended or adjusted under 35 U.S.C. 154(b) by 0 days.

(21) Appl. No.: 15/541,736

(22) PCT Filed: Feb. 9, 2016

(86) PCT No.: PCT/JP2016/053857
§ 371 (c)(1),
(2) Date: Jul. 6, 2017

(87) PCT Pub. No.: WO2016/132975
PCT Pub. Date: Aug. 25, 2016

(65) Prior Publication Data
US 2018/0002359 A1    Jan. 4, 2018

(30) Foreign Application Priority Data

Feb. 17, 2015 (JP) ................. 2015-028807

(51) Int. Cl.
*C07C 39/19*    (2006.01)
*C07F 9/6574*   (2006.01)
*C08K 5/526*    (2006.01)

(52) U.S. Cl.
CPC .......... *C07F 9/65744* (2013.01); *C07C 39/19* (2013.01); *C08K 5/526* (2013.01)

(58) Field of Classification Search
CPC .............. C07F 9/65744; C07C 39/19
See application file for complete search history.

(56) References Cited

U.S. PATENT DOCUMENTS 5,889,095 A * 3/1999 Inui ............... C07F 9/65744
524/117

FOREIGN PATENT DOCUMENTS

| JP | 5-86084 A    | 4/1993  |
| JP | 10-273494 A  | 10/1998 |
| JP | 3876479 B2   | 1/2007  |

OTHER PUBLICATIONS

Song et al. Tetrahedron 2015, 71, 3603-3608.*
English translation of the International Preliminary Report on Patentability dated Aug. 22, 2017 in counterpart international application No. PCT/JP2016/053857.
International Search Report dated May 17, 2016 issued by the International Searching Authority in corresponding application No. PCT/JP2016/053857.
Song et al., "Toward the Synthesis of Hirsutellone B via an Intramolecular Diels-Alders/Ketene-Trapping Strategy", Tetrahedron, vol. 71, 2015, pp. 3603-3608. (6 pages total).
Office Action dated Sep. 19, 2017 in corresponding Korean Application No. 10-2017-7014321.

* cited by examiner

*Primary Examiner* — Matthew P Coughlin
(74) *Attorney, Agent, or Firm* — Sughrue Mion, PLLC

(57) ABSTRACT

The present invention relates to a novel phosphite compound represented by the formula (I):

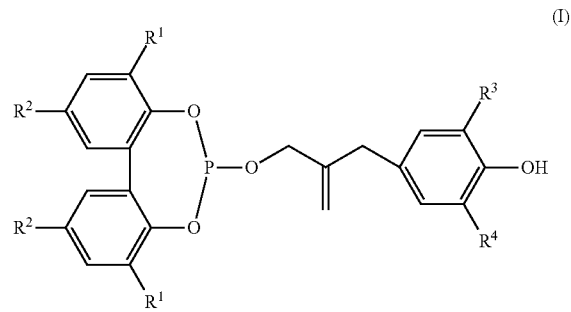

(I)

wherein $R^1$, $R^2$, $R^3$ and $R^4$ each independently represent a hydrogen atom, an alkyl group having 1 to 8 carbon atoms, a cycloalkyl group having 5 to 8 carbon atoms, an alkylcycloalkyl group having 6 to 12 carbon atoms, an aralkyl group having 7 to 12 carbon atoms, or an aryl group having 6 to 12 carbon atoms, a process for producing the same, and uses thereof as a stabilizer for an organic material.

12 Claims, No Drawings

PHOSPHITE COMPOUND, METHOD FOR PRODUCING THE SAME AND USES THEREOF

CROSS REFERENCE TO RELATED APPLICATIONS

This application is a National Stage of International Application No. PCT/JP2016/053857 filed Feb. 9, 2016, claiming priority based on Japanese Patent Application No. 2015-028807 filed Feb. 17, 2015, the contents of all of which are incorporated herein by reference in their entirety.

TECHNICAL FIELD

This patent application claims priority to Japanese Patent Application No. 2015-028807 (filed on Feb. 17, 2015), which is incorporated herein by reference in its entirety.

The present invention relates to a novel phosphite compound, a method for producing the same, and uses thereof as a stabilizer for an organic material.

BACKGROUND ART

Organic materials such as thermoplastic resins, thermosetting resins, natural or synthetic rubbers, mineral oils, lubricating oils, adhesives, paints, etc. may deteriorate due to the action of heat, oxygen, etc. during production, processing and also use thereof, which leads to reduction of strength properties, flowability change, coloring, deterioration of surface physical properties, and the like of the organic material. It is known that the commercial value is significantly impaired as the result.

Various phenolic antioxidants and phosphorus antioxidants have hitherto been developed for the purpose of preventing such deterioration due to heat or oxygen and it is known that by adding these to the organic material, the organic material can be stabilized (Patent Documents 1 and 2).

Patent Document 1: JP-A-5-86084
Patent documents 2: JP-B-3876479

SUMMARY OF INVENTION

Problems to be Solved by the Invention

Conventionally used phosphorus antioxidants sometimes have insufficient stabilizing effect against deterioration due to heat or oxygen during processing of organic materials, and there is a need for compounds having further stabilizing effects.

An object of the present invention is to provide a novel compound which is effective for improving thermal stability when processing an organic material.

Means for Solving the Problems

In order to solve the above problems, the present inventors have extensively studied phosphite ester compounds to find novel phosphite compounds and hydroxy compounds, and have completed the present invention.

That is, the present invention includes the following preferable aspects.

[1] A phosphite compound represented by the formula (I)

[Formula 1]

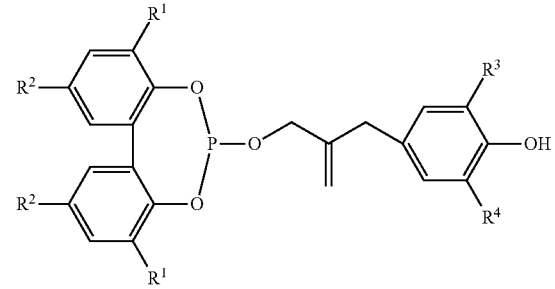

wherein $R^1$, $R^2$, $R^3$ and $R^4$ each independently represent a hydrogen atom, an alkyl group having 1 to 8 carbon atoms, a cycloalkyl group having 5 to 8 carbon atoms, an alkyl cycloalkyl group having 6 to 12 carbon atoms, an aralkyl group having 7 to 12 carbon atoms or an aryl group having 6 to 12 carbon atoms.

[2] A hydroxy compound represented by the formula (II)

[Formula 2]

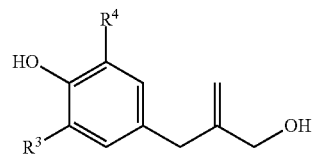

wherein $R^3$ and $R^4$ are as defined above.

[3] A method for producing the phosphite compound according to the above [1], wherein the hydroxy compound represented by the formula (II), a bisphenol compound represented by the formula (III)

[Formula 3]

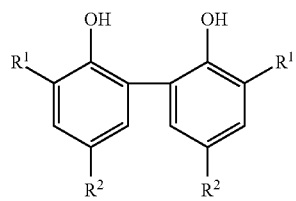

wherein $R^1$ and $R^2$ are as defined above,
and a phosphorus trihalide are reacted.

[4] A stabilizer for an organic material, comprising the phosphite compound according to [1].

[5] The stabilizer according to the above [4], wherein the organic material is a thermoplastic resin.

[6] The stabilizer according to the above [5], wherein the thermoplastic resin is a polyolefin or an engineering plastic.

[7] A method for stabilizing an organic material, wherein the phosphite compound according to the above [1] is added to an organic material.

[8] The method according to the above [7], wherein the organic material is a thermoplastic resin.

[9] The method according to the above [8], wherein the thermoplastic resin is a polyolefin or an engineering plastic.

[10] A stabilized organic material composition, comprising an organic material and the phosphite compound according to the above [1].

[11] The composition according to the above [10], wherein the organic material is a thermoplastic resin.

[12] The composition according to the above [11], wherein the thermoplastic resin is a polyolefin or an engineering plastic.

Effects of the Invention

The phosphite compound of the present invention is effective for improving the thermal stability in processing an organic material such as a thermoplastic resin.

MODE FOR CARRYING OUT THE INVENTION

The present invention provides the phosphite compound represented by the formula (I):

[Formula 4]

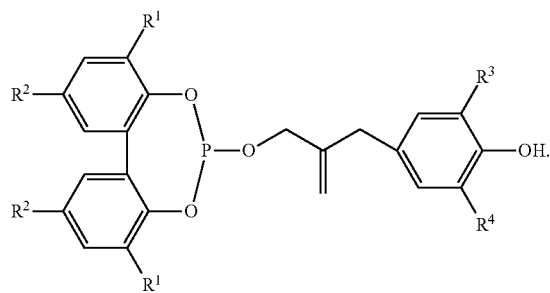

(I)

The symbols in the above formula (I) will be described.

$R^1$, $R^2$, $R^3$ and $R^4$ each independently represent a hydrogen atom, an alkyl group having 1 to 8 carbon atoms, a cycloalkyl group having 5 to 8 carbon atoms, an alkylcycloalkyl group having 6 to 12 carbon atoms, an aralkyl group having 7 to 12 carbon atoms or an aryl group having 6 to 12 carbon atoms. The two $R^1$s in the formula (I) may be the same group or different groups from each other. The two $R^2$s in the formula (I) may also be the same group or different groups from each other.

Examples of the alkyl group having 1 to 8 carbon atoms include a methyl group, an ethyl group, an n-propyl group, an i-propyl group, an n-butyl group, an i-butyl group, a sec-butyl group, a t-butyl group, a t-pentyl group, an i-octyl group, a t-octyl group, a 2-ethylhexyl group and the like.

Examples of the cycloalkyl group having 5 to 8 carbon atoms include a cyclopentyl group, a cyclohexyl group, a cycloheptyl group, a cyclooctyl group and the like.

Examples of the alkylcycloalkyl group having 6 to 12 carbon atoms include a 1-methylcyclopentyl group, a 1-methylcyclohexyl group, a 1-methyl-4-i-propylcyclohexyl group and the like.

Examples of the aralkyl group having 7 to 12 carbon atoms include a benzyl group, an α-methylbenzyl group, an α,α-dimethylbenzyl group and the like.

Examples of the aryl group having 6 to 12 carbon atoms include a phenyl group, a naphthyl group, tolyl group, a xylyl group and the like.

It is preferable that $R^1$, $R^2$ and $R^3$ are each independently an alkyl group having 1 to 8 carbon atoms, a cycloalkyl group having 5 to 8 carbon atoms, or an alkyl cycloalkyl group having 6 to 12 carbon atoms.

More preferably, $R^1$ and $R^3$ are each independently a t-alkyl group such as a t-butyl group, a t-pentyl group, and a t-octyl group, a cyclohexyl group or a 1-methylcyclohexyl group.

$R^2$s are each independently, preferably, an alkyl group having 1 to 5 carbon atoms such as a methyl group, an ethyl group, an n-propyl group, an i-propyl group, an n-butyl group, an i-butyl group, a sec-butyl group, a t-butyl group, a t-pentyl group and the like, and more preferably, a methyl group, a t-butyl group or a t-pentyl group.

$R^4$ is preferably a hydrogen atom, an alkyl group having 1 to 8 carbon atoms or a cycloalkyl group having 5 to 8 carbon atoms, more preferably, an alkyl group having 1 to 5 carbon atoms such as a methyl group, an ethyl group, an n-propyl group, an i-propyl group, an n-butyl group, an i-butyl group, a sec-butyl group, a t-butyl group, and a t-pentyl group, or a hydrogen atom, further preferably, a methyl group.

In the above-mentioned formula (I),
preferably, $R^1$ and $R^3$ are each independently a t-alkyl group, $R^2$s are independently an alkyl group having 1 to 5 carbon atoms, $R^4$ is an alkyl group having 1 to 5 carbon atoms or a hydrogen atom,
more preferably, $R^1$ and $R^3$ are each independently a t-butyl group, a t-pentyl group or a t-octyl group, $R^2$s are each independently a methyl group, a t-butyl group or a t-pentyl group, $R^4$ is a methyl group, an ethyl group, an n-propyl group, an i-propyl group, an n-butyl group, an i-butyl group, a sec-butyl group, a t-butyl group or a t-pentyl group,
further preferably, $R^1$ and $R^3$ are each independently a t-butyl group, a t-pentyl group or a t-octyl group, and $R^2$s are each independently a methyl group, a t-butyl group or a t-pentyl group, and $R^4$ is a methyl group.

Examples of the phosphite compound represented by the formula (I) include 2-t-butyl-6-methyl-4-(2-{[(2,4,8,10-tetra-t-butyldibenzo[d,f][1,3,2]dioxaphosphepin-6-yl)oxy]methyl}prop-2-en-1-yl)phenol, 2,6-di-t-butyl-4-(2-{[(2,4,8,0-tetra-t-butyldibenzo[d,f][1,3,2]dioxaphosphepin-6-yl)oxy]methyl}prop-2-en-1-yl)phenol, 2-t-butyl-6-ethyl-4-(2-{[(2,4,8,10-tetra-t-butyldibenzo[d,f][1,3,2]dioxaphosphepin-6-yl)oxy]methyl}prop-2-en-1-yl)phenol and the like.

The phosphite compound represented by the above formula (I) can be produced, for example, by reacting a hydroxy compound represented by the formula (II):

[Formula 5]

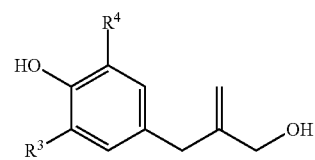

(II)

wherein $R^3$ and $R^4$ are as defined above,
a bisphenol compound represented by the formula (III):

[Formula 6]

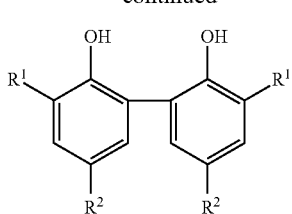

(III)

wherein R¹ and R² are as defined above,
and a phosphorus trihalide.

Examples of the phosphorus trihalide include phosphorus trichloride, phosphorus tribromide, and the like. In particular, phosphorus trichloride is preferably used.

In reacting the hydroxy compound represented by the formula (II), the bisphenol compound represented by the formula (III) and a phosphorus trihalide, for example, the reaction may be accelerated by coexisting dehydrohalogenation agents such as amines, pyridines, pyrrolidines, amides, etc., or hydroxides of alkali metals or alkaline earth metals. In order to accelerate the reaction, one type of dehydrohalogenation agent or an alkali metal or alkaline earth metal hydroxide may be used, or two or more of these may be used in combination.

As amines, any of primary amines, secondary amines, and tertiary amines may be used. Examples of the amines include t-butylamine, t-pentylamine, t-hexylamine, t-octylamine, di-t-butylamine, di-t-pentylamine, di-t-hexylamine, di-t-octylamine, trimethylamine, triethylamine, N,N-diisopropylethylamine, N,N-dimethylaniline, N,N-diethylaniline and the like. Triethylamine and/or N,N-diisopropylethylamine are preferably used as amines from the viewpoint of easily accelerating the reaction. Examples of pyridines include pyridine, picoline and the like, and pyridine is preferably used. Examples of pyrrolidines include 1-methyl-2-pyrrolidine and the like. Examples of the amides include N,N-dimethylformamide, N,N-dimethylacetamide and the like, and N,N-dimethylformamide is preferably used.

Examples of the alkali metal or alkaline earth metal hydroxide include sodium hydroxide, calcium hydroxide and the like, and sodium hydroxide is preferably used.

The reaction is usually carried out in an organic solvent. The organic solvent is not particularly limited as long as it does not inhibit the reaction, and examples thereof include aromatic hydrocarbons, aliphatic hydrocarbons, oxygen-containing hydrocarbons, halogenated hydrocarbons and the like. The reaction may be carried out in one type of organic solvent, in a mixed solvent of two or more kinds of organic solvents, or in a mixed solvent of the organic solvent and another solvent.

Examples of the aromatic hydrocarbons include benzene, toluene, xylene, ethylbenzene and the like. Examples of aliphatic hydrocarbons include n-hexane, n-heptane, n-octane and the like. Examples of the oxygen-containing hydrocarbons include diethyl ether, dibutyl ether, tetrahydrofuran, 1,4-dioxane and the like. Examples of the halogenated hydrocarbons include chloroform, carbon tetrachloride, monochlorobenzene, dichloromethane, 1,2-dichloroethane, dichlorobenzene and the like.

From the viewpoint of improving the yield, it is preferable to use toluene, xylene, n-hexane, n-heptane, diethyl ether, tetrahydrofuran, 1,4-dioxane, chloroform or dichloromethane as the organic solvent.

As a reaction method, a two-step reaction method is usually adopted in which first, a bisphenol compound represented by the formula (III) is reacted with phosphorus trihalide to form an intermediate, and then the intermediate is reacted with a hydroxy compound represented by the formula (II).

In this method, a phosphorus trihalide is used preferably in an amount of about 1 to 1.1 molar times, more preferably in an amount of about 1 to 1.05 molar times relative to the bisphenol compound represented by formula (III). When a dehydrohalogenation agent is used, the dehydrohalogenation agent is used in an amount of about 0.05 to 2.4 molar times, more preferably 2 to 2.1 molar times, relative to phosphorus trihalide The reaction between the bisphenol compound represented by the formula (III) and a phosphorus trihalide is usually carried out at a temperature of about 0 to 200° C. It is considered that this reaction produces a halogenophosphite as an intermediate. The produced intermediate may be isolated and subjected to the next reaction, but usually it is subjected to reaction with the hydroxy compound represented by the formula (II) as it is.

In the subsequent reaction with the hydroxy compound represented by the formula (II), the hydroxy compound represented by the formula (II) is used usually in an amount of about 1 to 1.1 molar times relative to the bisphenol compound represented by the formula (III).

Also in this reaction, a dehydrohalogenation agent can be used. In this case, the amount of the dehydrohalogenation agent is preferably about 0.05 to 1.2 molar times relative to the hydroxy compound represented by the formula (II). In this regard, when the dehydrohalogenation agent is used in an excessive amount in the first reaction, the amount of the dehydrohalogenation agent is usually calculated as the total amount of the remaining dehydrohalogenation agent and the added dehydrohalogenation agent. The reaction with the hydroxy compound represented by the formula (II) is usually carried out at a temperature of about 0 to 200° C.

In the case of using a dehydrohalogenation agent, the hydrohalic acid salt of the dehydrohalogenation agent formed by the reaction is removed after completion of the reaction, and the solvent is further removed, and then, the phosphite compound of the present invention represented by the formula (I) can be obtained by being subjected to a suitable post treatment such as crystallization or column chromatography.

The present invention also provides a hydroxy compound represented by the above formula (II) which can be used as an intermediate for producing a phosphite compound represented by the formula (I). Furthermore, the present invention provides a method for producing a phosphite compound represented by the formula (I), characterized in that the method comprises reacting a hydroxy compound represented by the formula (II), a bisphenol compound represented by the formula (III), and phosphorus trihalide.

The hydroxy compound represented by the formula (II) used in the production method of the present invention can be produced according to the following scheme 1.

Examples of the hydroxy compound represented by the formula (II) include 2-t-butyl-4-[2-(hydroxymethyl)prop-2-en-1-yl]-6-methylphenol, 2-t-butyl-6-ethyl-4-[2-(hydroxymethyl)prop-2-en-1-yl]phenol, 2,6-di-t-butyl-4-[2-(hydroxymethyl)prop-2-en-1-yl]phenol and the like.

The bisphenol compound represented by the formula (III) used in the production method of the present invention can be produced by a known method, for example, by condensing alkylphenols in accordance with the method described in JP-A-52-122350, U.S. Pat. No. 2,538,355, JP-B-2-47451 or Scheme 1

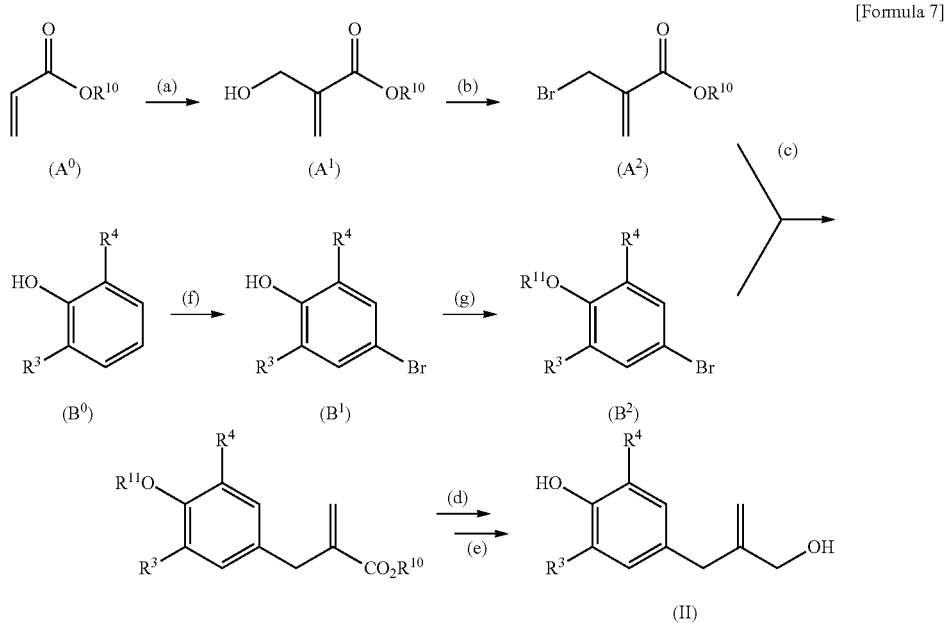

[Formula 7]

Scheme 1 will be described. First, a kind of various phenols (a compound represented by the formula (Bo)) is brominated (step (f)), a phenolic hydroxyl group is protected with methyl iodide or the like (step (g)) for example, to produce a compound represented by the formula ($B^2$). The obtained compound represented by the formula ($B^2$) is subjected to Grignard reaction with the compound represented by the formula ($A^2$) (e.g., ethyl-2-(bromomethyl)prop-2-enoate, a compound wherein R10 in the formula ($A^2$) is an ethyl group), for example, (step (c)) to produce an ester compound, and by subjecting the ester compound to reduction (step (d)) and deprotecting group (step (e)), the hydroxy compound represented by the formula (II) can be produced.

Examples of the reducing agent used in the step (d) include aluminum lithium hydride, aluminum sodium hydride, lithium borohydride, sodium borohydride, calcium borohydride, aluminum sodium triethoxyhydride, sodium triacetoxyborohydride, tributyltin hydride, 9-BBN-pyridine, boron trihydride, sodium, sodium/ammonia in the coexistence of alcohol, lithium/ammonia in the coexistence of alcohol, di-iso-butylaluminum hydride.

A compound represented by the formula ($A^2$) (e.g., ethyl-2-(bromomethyl)prop-2-enoate) can be produced by reacting a compound represented by the formula ($A^0$) (e.g., ethyl acrylate) with paraformaldehyde to prepare a compound represented by the formula ($A^1$) (step (a)), followed by bromination (step (b)).

the like. Also, when a bisphenol compound represented by the above formula (III) is commercially available, it can also be used.

Examples of the bisphenol compound represented by the formula (III) include biphenyl-2,2'-diol, 3,3',5,5'-tetra-t-butylbiphenyl-2,2'-diol, 3,3'-dimethyl-5,5'-di-t-butylbiphenyl-2,2'-diol and the like.

The hydrolysis resistance of the phosphite compound can also be improved by adding an amine, an acid-binding metal salt or the like to the phosphite compound of the present invention represented by the formula (I).

Examples of such amines include trialkanolamines such as triethanolamine, tripropanolamine and tri-i-propanolamine, dialkanolamines such as diethanolamine, dipropanolamine, di-i-propanolamine, tetraethylethylene diamine, tetra-i-propanol and ethylenediamine, monoalkanol amines such as dibutylethanolamine and dibutyl-i-propanolamine, alkyl amines such as dibutylamine, piperidine, 2,2,6,6-tetramethylpiperidine, 4-hydroxy-2,2,6,6-tetramethylpiperidine, bridged cyclic amines such as hexamethylenetetramine and triethylenediamine, polyalkylenepolyamines such as triethylenetetramine, tetraethylenepentamine, hindered amine light stabilizers described later, and the like.

Further, long-chain aliphatic amines described in JP-A-61-63686, compounds containing a sterically hindered amine group described in JP-A-6-329830, hindered piperidinyl light stabilizers described in JP-A-7-90270, organic amines described in JP-A-7-278164, and the like can also be used.

The use ratio of the amines is usually about 0.01 to 25% by mass based on the total amount of the phosphite compound represented by the formula (I).

Examples of acid-binding metal salts include hydrotalcites and the like. Examples of the hydrotalcite include a double salt compound represented by the following formula.

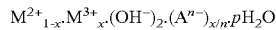
$$M^{2+}{}_{1-x}\cdot M^{3+}{}_{x}\cdot(OH^-)_2\cdot(A^{n-})_{x/n}\cdot pH_2O$$

[In the formula, $M^{2+}$ represents $Mg^{2+}$, $Ca^{2+}$, $Sr^{2+}$, $Ba^{2+}$, $Zn^{2+}$, $Pb^{2+}$, $Sn^{2+}$ and/or $Ni^{2+}$; $M^{3+}$ represents $Al^{3+}$, $B^{3+}$ or $Bi^{3+}$; n represents a number from 1 to 4, x represents a number from 0 to 0.5, and p represents a number from 0 to 2. $A^{n-}$ represents an anion of valence n.]

Specific examples of the anion having a valency n represented by $A^{n-}$ include $OH^-$, $Cl^-$, $Br^-$, $I^-$, $ClO_4^-$, $HCO_3^-$, $C_6H_5COO^-$, $CO_3^{2-}$, $SO^{2-}$, $-OCOCO^-$, $(CHOHCOO)_2^{2-}$, $C_2H_4(COO)_2^{2-}$, $(CH_2COO)_2^{2-}$, $CH_3CHOHCOO^-$, $SiO_3^{3-}$, $SiO_4^{4-}$, $Fe(CN)_6^{4-}$, $BO^{3-}$, $PO_3^{3-}$, $HPO_4^{2-}$ and the like.

Among the hydrotalcites represented by the above formula, hydrotalcites represented by the following formulas are more preferable.

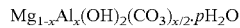
$$Mg_{1-x}Al_x(OH)_2(CO_3)_{x/2}\cdot pH_2O$$

[In the formula, x and p are as defined above.]

The hydrotalcite may be a natural product or a synthetic product and may be used regardless of its crystal structure, crystal particle diameter and the like.

In addition, ultrafine zinc oxides described in JP-A-6-329830, inorganic compounds described in JP-A-7-278164 and the like can also be used as acid-binding metal salts.

The use ratio of the acid-binding metal salt is usually about 0.01 to 25% by mass based on the total amount of the phosphite compound represented by the formula (I).

By adding the phosphite compound of the present invention represented by the formula (I) to the organic material, it is possible to reduce thermal deterioration, oxidative deterioration, etc. of the organic material and stabilize the organic material. Therefore, the phosphite compound of the present invention is suitable as an active ingredient of a stabilizer for an organic material.

The present invention also provides a stabilizer for an organic material, comprising the phosphite compound of the present invention represented by the formula (I), a method for stabilizing an organic material, wherein the phosphite compound of the present invention represented by the formula (I) is added to an organic material, and, a stabilized organic material composition, comprising an organic material and the phosphite compound of the present invention represented by formula (I). In these embodiments, as the phosphite compound of the present invention represented by the formula (I), one type of the phosphite compound represented by the formula (I) may be used, or two or more of the phosphite compounds represented by the formula (I) may be used in combination.

Examples of the organic material that can be stabilized by the phosphite compound of the present invention include the following, but it is not limited to these organic materials. The organic material may be one kind of an organic material or a mixture of two or more kinds of organic materials.
(1) Polyethylene such as high density polyethylene (HD-PE), low density polyethylene (LD-PE), linear low density polyethylene (LLDPE),
(2) Polypropylene,
(3) Methylpentene polymer,
(4) EAA (ethylene/ethyl acrylate copolymer) resin,
(5) Ethylene/vinyl acetate copolymer resin,
(6) Polystyrenes such as polystyrene, poly(p-methylstyrene), poly (α-methylstyrene),
(7) AS (acrylonitrile/styrene copolymer) resin,
(8) ABS (acrylonitrile/butadiene/styrene copolymer) resin,
(9) AAS (special acrylic rubber/acrylonitrile/styrene copolymer) resin,
(10) ACS (acrylonitrile/chlorinated polyethylene/styrene copolymer) resin,
(11) Chlorinated polyethylene, polychloroprene, chlorinated rubber,
(12) Polyvinyl chloride, polyvinylidene chloride,
(13) Methacrylic resin,
(14) Ethylene/vinyl alcohol copolymer resin,
(15) Fluororesin,
(16) Polyacetal,
(17) Grafted polyphenylene ether resin and polyphenylene sulfide resin,
(18) Polyurethane,
(19) Polyamide,
(20) Polyester resin such as polyethylene terephthalate, polybutylene terephthalate,
(21) Polycarbonate,
(22) Polyacrylate,
(23) Polysulfone, polyether ether ketone, polyether sulphone,
(24) Thermoplastic resins, such as aromatic polyester resin,
(25) Epoxy resin,
(26) Diallyl phthalate prepolymer,
(27) Silicone resin,
(28) Unsaturated polyester resin,
(29) Acrylic modified benzoguanamine resin,
(30) Benzoguanamine/melamine resin,
(31) Thermosetting resins, such as urea resin,
(32) Polybutadiene,
(33) 1,2-Polybutadiene,
(34) Polyisoprene,
(35) Styrene/butadiene copolymer,
(36) Butadiene/acrylonitrile copolymer,
(37) Ethylene/propylene copolymer,
(38) Silicone rubber,
(39) Epichlorhydrin rubber,
(40) Acrylic rubber,
(41) Natural rubber,
(42) Chlorine rubber type paint,
(43) Polyester resin paint,
(44) Urethane resin paint,
(45) Epoxy resin paint,
(46) Acrylic resin paint,
(47) Vinyl resin paint,
(48) Amino alkyd resin paint,
(49) Alkyd resin paint,
(50) Nitrocellulose resin paint,
(51) Oil paint,
(52) Wax,
(53) Lubricating oil and so on.

Among them, thermoplastic resins, particularly polyethylene, for example, polyolefins such as HD-PE, LD-PE, LLDPE and polypropylene, engineering plastics such as polyamide, polyethylene terephthalate, polybutylene terephthalate and polycarbonate, and the like are preferably used.

The polyolefin is not particularly limited, and may be, for example, one obtained by radical polymerization or may be one produced by polymerization using a catalyst containing a metal of group IVb, Vb, VIb or VIII of the periodic table. Examples of the catalyst containing such a metal include a metal complex having one or more ligands, for example, an oxide, a halogen compound, an alcoholate, an ester, and an aryl coordinated by a n or a bond. These complexes may be used as they are, or they may be supported on a substrate such as magnesium chloride, titanium chloride, alumina, silicon oxide or the like. As the polyolefin, for example, one produced by using a Ziegler-Natta catalyst, a TNZ catalyst, a metallocene catalyst, a Phillips catalyst or the like is preferably used.

Engineering plastics are also not particularly limited. The polyamide resin is one having an amide bond in the polymer chain, and may be anything as long as it can be heated and melted. The polyamide resin may be produced by any method, for example, one produced by a condensation reaction of a diamine and a dicarboxylic acid, a condensation reaction of an aminocarboxylic acid, a ring-opening polymerization of a lactam or the like. Examples of the polyamide resin include nylon 66, nylon 69, nylon 610, nylon 612, poly-bis-(p-aminocyclohexyl)methandodecamide, nylon 46, nylon 6, nylon 12, Nylon 66/6 which is a copolymer of nylon 66 and nylon 6, nylon 6/12 and the like. The polyester resin is one having an ester bond in the polymer chain and may be anything as long as it can be heated and melted. Examples thereof include a polyester obtained by polycondensation of a dicarboxylic acid and a dihydroxy compound or the like. The polyester resin may be either a homopolyester or a copolyester. The polycarbonate resin is one having a carbonate bond in the polymer chain and may be anything as long as it can be heated and melted. Examples thereof include a polycarbonate resin obtained by reacting an aromatic hydroxy compound or additionally to this a small amount of a polyhydroxy compound with a carbonate precursor such as phosgene or diphenyl carbonate in the presence of a solvent, an acid acceptor, or a molecular weight regulator. The polycarbonate resin may be linear, branched, or may be a copolymer.

When the organic material is stabilized by adding the phosphite compound of the present invention represented by the formula (I) to the organic material, the content of the phosphite compound of the present invention is, from the viewpoint of stabilizing the organic material, usually 0.0001 part by mass or more, preferably 0.001 part by mass or more, more preferably 0.01 part by mass or more, further more preferably 0.05 part by mass or more, based on 100 parts by mass of the organic material. The content of the phosphite compound of the present invention is usually 5 parts by mass or less, preferably 3 parts by mass or less, more preferably 1 part by mass or less, based on 100 parts by mass of the organic material from the viewpoint of efficiently stabilizing the organic material and from the economical viewpoint.

In adding the phosphite compound of the present invention represented by formula (I) to the organic material, further additives can be added to the organic material as needed, and examples of the additive include phenolic antioxidants, sulfur-based antioxidants, phosphorus antioxidants, ultraviolet absorbers, light stabilizers, peroxide scavengers, polyamide stabilizers, hydroxylamines, lubricants, plasticizers, flame retardants, nucleating agents, metal deactivators, antistatic agents, pigments, fillers, antiblocking agents, surfactants, processing aids, foaming agents, emulsifiers, brighteners, calcium stearate, neutralizers such as hydrotalcite, further, color improvers such as 9,10-dihydro-9-oxa-10-phosphophenanthrene-10-oxide, supplementary stabilizers such as benzofurans and indolines described in U.S. Pat. No. 4,325,853, U.S. Pat. No. 4,338,244, U.S. Pat. No. 5,175,312, U.S. Pat. No. 5,216,053, U.S. Pat. No. 5,252,643, U.S. Pat. No. 4,316,611, DE-A-4,316,622, DE-A-4,316,876, EP-A-589,839, and EP-A-591,102, and the like. These additives can be added to the organic material simultaneously with the phosphite compound of the present invention or can be added to the organic material at a stage different from the phosphite compound of the present invention. As the additives, one kind of additives may be used, or two or more kinds of additives may be used in combination.

Examples of the phenolic antioxidant include the followings. As the phenolic antioxidant, the following compounds may be used alone, or two or more of them may be used in combination.

(1) Examples of Alkylated Monophenols 2,6-Di-t-butyl-4-methylphenol, 2,4,6-tri-t-butylphenol, 2,6-di-t-butylphenol, 2-t-butyl-4,6-dimethylphenol, 2,6-di-t-butyl-4-ethylphenol, 2,6-di-t-butyl-4-n-butylphenol, 2,6-di-t-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-t-butyl-4-methoxymethylphenol, 2,6-di-nonyl-4-methylphenol, 2,4-dimethyl-6-(1'-methylundecyl-1'-yl)phenol, 2,4-dimethyl-6-(1'-methylheptadecyl-1'-yl)phenol, 2,4-dimethyl-6-(1'-methyl tridecyl-1'-yl)phenol and any mixtures thereof.

(2) Examples of Alkylthiomethylphenols 2,4-Dioctylthiomethyl-6-t-butylphenol, 2,4-dioctylthiomethyl-6-methylphenol, 2,4-dioctylthiomethyl-6-ethylphenol, 2,6-didodecylthiomethyl-4-nonylphenol and any mixtures thereof.

(3) Examples of Hydroquinone and Alkylated Hydroquinones 2,6-Di-t-butyl-4-methoxyphenol, 2,5-di-t-butylhydroquinone, 2,5-di-t-amylhydroquinone, 2,6-diphenyl-4-octadecyloxyphenol, 2,6-di-t-butylhydroquinone, 2,5-di-t-butyl-4-hydroxyanisole, 3,5-di-t-butyl-4-hydroxyphenylstearate, bis(3,5-di-t-butyl-4-hydroxyphenyl)adipate and any mixtures thereof.

(4) Examples of Tocopherols

α-Tocopherol, β-tocopherol, γ-tocopherol, δ-tocopherol and any mixtures thereof.

(5) Examples of Hydroxylated Thiodiphenyl Ethers 2,2'-Thiobis(6-t-butylphenol), 2,2'-thiobis(4-methyl-6-t-butylphenol), 2,2'-thiobis(4-octylphenol), 4,4'-thiobis(3-methyl-6-t-butylphenol), 4,4'-thiobis(2-methyl-6-t-butylphenol), 4,4'-thiobis(3,6-di-t-amylphenol), 4,4'-(2,6-dimethyl-4-hydroxyphenyl)disulfide and the like.

(6) Examples of Alkylidene Bisphenols and Derivatives Thereof 2,2'-Methylenebis(4-methyl-6-t-butylphenol), 2,2'-methylenebis(4-ethyl-6-t-butylphenol), 2,2'-methylenebis[4-methyl-6-(α-methylcyclohexyl)phenol]], 2,2'-methylenebis(4-methyl-6-cyclohexylphenol), 2,2'-methylenebis(4-methyl-6-nonylphenol), 2,2'-methylenebis(4,6-di-t-butylphenol), 2,2'-ethylidenebis(4,6-di-t-butylphenol), 2,2'-ethylidenebis(4-isobutyl-6-t-butylphenol), 2,2'-methylenebis[6-(α-methylbenzyl)-4-nonylphenol], 2,2'-methylenebis[4,6-(α,α-dimethylbenzyl)-4-nonylphenol], 4,4'-methylenebis(6-t-butyl-2-methylphenol), 4,4'-methylenebis(2,6-di-t-butylphenol), 4,4'-butylidenebis(3-methyl-6-t-butylphenol), 1,1-bis(4-hydroxyphenyl)cyclohexane, 1,1-bis(5-t-butyl-4-hydroxy-2-methylphenyl)butane, 2,6-bis(3-t-butyl-5-methyl-2-hydroxybenzyl)-4-methylphenol, 1,1,3-tris(5-t-butyl-4-hydroxy-2-methylphenyl) butane, 1,1-bis(5-t-butyl-4-hydroxy-2-methylphenyl)-3-n-dodecylmercaptobutane, ethyleneglycolbis[3,3-bis-3'-butyl-4'-hydroxyphenyl)butyrate], bis(3-t-butyl-4-hydroxy-5- methylphenyl)dicyclopentadiene, bis[2-(3'-t-butyl-2'-hydroxy-5'-methylbenzyl)-6-t-butyl-4-methylphenyl] terephthalate, 1,1-bis(3,5-dimethyl-2-hydroxyphenyl) butane, 2,2-bis(3,5-di-t-butyl-4-hydroxyphenyl)propane, 2,2-bis(5-t-butyl-4-hydroxy-2-methylphenyl)-4-n-dodecyl-mercaptobutane, 1,1,5,5-tetra(5-t-butyl-4-hydroxy-2-methylphenyl)pentane, 2-t-butyl-6-(3'-t-butyl-2'-hydroxybenzyl)-4-methylphenylacrylate, 2,4-di-t-pentyl-6-[1-(2-hydroxy-3,5-di-t-pentylphenyl)ethyl]phenylacrylate and any mixtures thereof.

(7) Examples of O-, N- and S-Benzyl Derivatives 3,5,3',5'-Tetra-t-butyl-4,4'-dihydroxydibenzylether, octadecyl-4-hydroxy-3,5-dimethylbenzylmercaptoacetate, tris(3,5-di-t-butyl-4-hydroxybenzyl)amine, bis(4-t-butyl-3-hydroxy-2,6-dimethylbenzyl)dithioterephthalate, bis(3,5-di-t-butyl-4-hydroxybenzyl)sulfide, isooctyl-3,5-di-t-butyl-4-hydroxybenzylmercaptoacetate and any mixtures thereof.

(8) Examples of Hydroxybenzylated Malonate Derivatives

Dioctadecyl-2,2-bis(3,5-di-t-butyl-2-hydroxybenzyl)malonate, dioctadecyl 2-(3-t-butyl-4-hydroxy-5-methylbenzyl) malonate, didodecylmercaptoethyl-2,2-bis(3,5-di-t-butyl-4-hydroxybenzyl)malonate, bis[4-(1,1,3,3-tetramethylbutyl)phenyl]-2,2-bis(3,5-di-t-butyl-4-hydroxybenzyl) malonate and any mixtures thereof.

(9) Examples of Aromatic Hydroxybenzyl Derivatives 1,3,5-Trimethyl-2,4,6-tris(3,5-di-t-butyl-4-hydroxybenzyl)benzene, 1,4-bis(3,5-di-t-butyl-4-hydroxybenzyl)-2,3,5,6-tetramethylbenzene, 2,4,6-tris(3,5-t-butyl-4-hydroxybenzyl)phenol and any mixtures thereof.

(10) Examples of Triazine Derivatives 2,4-Bis(n-octylthio)-6-(4-hydroxy-3,5-di-t-butylanilino)-1,3,5-triazine, 2-n-octylthio-4,6-bis(4-hydroxy-3,5-di-t-butylanilino)-1,3,5-triazine, 2-n-octylthio-4,6-bis(4-hydroxy-3,5-di-t-butylphenoxy)1,3,5-triazine, 2,4,6-tris(3,5-di-t-butyl-4-phenoxy)-1,3,5-triazine, tris(4-t-butyl-3-hydroxy-2,6-dimethylbenzyl)isocyanurate, tris(3,5-di-t-butyl-4-hydroxybenzyl)isocyanurate, 2,4,6-tris(3,5-di-t-butyl-4-hydroxyphenylethyl)-1,3,5-triazine, 2,4,6-tris(3,5-di-t-butyl-4-hydroxyphenylpropyl)-1,3,5-triazine, tris(3,5-dicyclohexyl-4-hydroxybenzyl)isocyanurate, tris[2-(3',5'-di-t-butyl-4'-hydroxycinnamoyloxy)ethyl] isocyanurate and any mixtures thereof.

(11) Examples of Benzylphosphonate Derivatives

Dimethyl-3,5-di-t-butyl-4-hydroxybenzylphosphonate, diethyl-3,5-di-t-butyl-4-hydroxybenzylphosphonate, dioctadecyl-3,5-di-t-butyl-4-hydroxybenzylphosphonate, dioctadecyl-5-t-butyl-4-hydroxy-3-methylbenzylphosphonate, calcium salt of 3,5-di-t-butyl-4-hydroxybenzylphosphonic acid monoester and any mixtures thereof.

(12) Examples of Acylaminophenol Derivatives

4-Hydroxyl lauric acid anilide, 4-hydroxystearic acid anilide, octyl-N-(3,5-di-t-butyl-4-hydroxyphenyl)carbanate and any mixtures thereof.

(13) Examples of Esters of β-(3,5-Di-t-Butyl-4-Hydroxyphenyl)Propionic Acid with the Following Monohydric or Polyhydric Alcohols Methanol, ethanol, octanol, octadecanol, ethylene glycol, 1,3-propanediol, 1,4-butanediol, 1,6-hexanediol, 1,9-nonanediol, neopentyl glycol, diethylene glycol, thioethylene glycol, spiroglycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylol propane, 4-hydroxymethyl-1-phospha-2,6,7-trioxabicyclo[2,2,2]octane and any mixtures thereof.

(14) Examples of Esters of β-(5-t-Butyl-4-Hydroxy-3-Methylphenyl)Propionic Acid with the Following Monohydric or Polyhydric Alcohols Methanol, ethanol, octanol, octadecanol, ethylene glycol, 1,3-propanediol, 1,4-butanediol, 1,6-hexanediol, 1,9-nonanediol, neopentyl glycol, diethylene glycol, thioethylene glycol, spiroglycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylol propane, 4-hydroxymethyl-1-phospha-2,6,7-trioxabicyclo[2,2,2]octane and any mixtures thereof.

(15) Examples of Esters of β-(3,5-Dicyclohexyl-4-Hydroxyphenyl)Propionic Acid with the Following Monohydric or Polyhydric Alcohols Methanol, ethanol, octanol, octadecanol, ethylene glycol, 1,3-propanediol, 1,4-butanediol, 1,6-hexanediol, 1,9-nonanediol, neopentyl glycol, diethylene glycol, thioethylene glycol, spiroglycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylol propane, 4-hydroxymethyl-1-phospha-2,6,7-trioxabicyclo[2,2,2]octane and any mixtures thereof.

(16) Examples of Esters of 3,5-Di-t-Butyl-4-Hydroxyphenylacetic Acid with the Following Monohydric or Polyhydric Alcohols Methanol, ethanol, octanol, octadecanol, ethylene glycol, 1,3-propanediol, 1,4-butanediol, 1,6-hexanediol, 1,9-nonanediol, neopentyl glycol, diethylene glycol, thioethylene glycol, spiroglycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylol propane, 4-hydroxymethyl-1-phospha-2,6,7-trioxabicyclo[2,2,2]octane and any mixtures thereof.

(17) Examples of Amides of β-(3,5-Di-t-Butyl-4-Hydroxyphenyl)Propionic Acid

N,N'-bis[3-(3',5'-di-t-butyl-4'-hydroxyphenyl)propionyl] hydrazine, N,N'-bis[3-(3',5'-di-t-butyl-4'-hydroxyphenyl)propionyl]hexamethylenediamine, N,N'-bis[3-(3',5'-di-t-butyl-4'-hydroxyphenyl)propionyl]trimethylenediamine and any mixtures thereof.

Examples of the sulfur-based antioxidant include the followings.

Dilauryl 3,3'-thiodipropionate, tridecyl 3,3'-thiodipropionate, dimyristyl 3,3'-thiodipropionate, distearyl 3,3'-thiodipropionate, laurylstearyl 3,3'-thiodipropionate, neopentanetetrayltetrakis(3-laurylthiopropionate) and the like.

Examples of the phosphorus antioxidant include the followings. As the phosphorus antioxidant, the following compounds may be used alone, or two or more of them may be used in combination.

Triphenyl phosphite, tris(nonylphenyl)phosphite, tris(2,4-di-t-butylphenyl)phosphite, trilaurylphosphite, trioctadecylphosphite, distearyl pentaerythritol diphosphite, diisodecyl pentaerythritol diphosphite, bis(2,4-di-t-butylphenyl)pentaerythritol diphosphite, bis(2,4-di-t-butyl-6-methylphenyl) pentaerythritol diphosphite, bis(2,6-di-t-butyl-4-methylphenyl)pentaerythritol diphosphite, bis(2,4,6-tri-t-butylphenyl) pentaerythritol diphosphite, tristearylsorbitol triphosphite, tetrakis(2,4-di-t-butylphenyl)-4,4'-diphenylenediphosphonite, 2,2'-methylenebis(4,6-di-t-butylphenyl) 2-ethylhexyl phosphite, 2,2'-ethylidenebis(4,6-di-t-butylphenyl)fluorophosphite, bis(2,4-di-t-butyl-6-methylphenyl)ethyl phosphite, bis(2,4-di-t-butyl-6-methylphenyl)methyl phosphite, 2-(2,4,6-tri-t-butylphenyl)-5-ethyl-5-butyl-1,3,2-oxaphosphorinane, 2,2',2''-nitrilo(triethyl-tris(3,3',5,5'-tetra-t-butyl-1,1'-biphenyl-2,2'-diyl)phosphite, 6-[3-(3-t-butyl-4-hydroxy-5-methylphenyl)propoxy]-2,4,8,10-tetra-t-butyldibenz[d,f][1,3,2]dioxaphosphepin and any mixtures thereof.

Examples of the ultraviolet absorber include the followings. As the ultraviolet absorber, the following compounds may be used alone, or two or more of them may be used in combination.

(1) Examples of Salicylate Derivatives

Phenyl salicylate, 4-t-butylphenyl salicylate, 2,4-di-t-butylphenyl 3',5'-di-t-butyl-4'-hydroxybenzoate, 4-t-octylphenyl salicylate, bis(4-t-butylbenzoyl)resorcinol, benzoyl resorcinol, hexadecyl 3',5'-di-t-butyl-4'-hydroxybenzoate, octadecyl 3',5'-di-t-butyl-4'-hydroxybenzoate, 2-methyl-4,6-di-t-butylphenyl 3',5'-di-t-butyl-4'-hydroxybenzoate and any mixtures thereof.

(2) Examples of 2-Hydroxybenzophenone Derivatives 2,4-Dihydroxybenzophenone, 2-hydroxy-4-methoxybenzophenone, 2-hydroxy-4-octoxybenzophenone, 2,2'-dihydroxy-4-methoxybenzophenone, bis(5-benzoyl-4-hydroxy-2-methoxyphenyl)methane, 2,2',4,4'-tetrahydroxybenzophenone and any mixtures thereof.

(3) Examples of 2-(2'-Hydroxyphenyl)Benzotriazole 2-(2'-hydroxy-5-methylphenyl)benzotriazole, 2-(3',5'-di-t-butyl-2'-hydroxyphenyl)benzotriazole, 2-(5'-t-butyl-2'-hydroxyphenyl)benzotriazole, 2-(2'-hydroxy-5'-t-octylphenyl) benzotriazole, 2-(3-t-butyl-2-hydroxy-5-methylphenyl)-5-chlorobenzotriazole, 2-(3'-s-butyl-2'-hydroxy-5'-t-butylphenyl)benzotriazole, 2-(2'-hydroxy-4'-octyloxyphenyl)benzotriazole, 2-(3',5'-di-t-amyl-2'-hydroxyphenyl)benzotriazole, 2-[2'-hydroxy-3',3'-bis(α,α-dimethylbenzyl)phenyl]-2H-benzotriazole, 2-[(3'-t-butyl-2'-hydroxyphenyl)-5'-(2-octyloxycarbonylethyl)phenyl]-5-chlorobenzotriazole, 2-[3'-t-butyl-5'-[2-(2-ethylhexyloxy) carbonylethyl]-2'-hydroxyphenyl]-5-chlorobenzotriazole, 2-[3'-t-butyl-3'-hydroxy-5'-(2-methoxycarbonylethyl)phenyl]-5-chlorobenzotriazole, 2-[3'-t-butyl-2'-hydroxy-5'-(2-methoxycarbonylethyl)phenyl]benzotriazole, 2-[3'-t-butyl-2'-hydroxy-5-(2-octyloxycarbonylethyl)phenyl] benzotriazole, 2-[3'-t-butyl-2'-hydroxy-5'-[2-(2-ethylhexyloxy)carbonylethyl]phenyl] benzotriazole, 2-[2-hydroxy-3-(3,4,5,6-tetrahydrophthalimidomethyl)-5-methylphenyl]benzotriazole, 2-(3,5-di-t-butyl-2-hydroxyphenyl)-5-chlorobenzotriazole, a mixture of 2-(3'-dodecyl-2'-hydroxy-5'-methylphenyl)benzotriazole and 2-[3'-t-butyl-2'-hydroxy-5'-(2-isooctyloxycarbonylethyl) phenyl]benzotriazole, 2,2'-methylenebis[6-(2H-benzotriazol-2-yl)-4-(1,1,3,3-tetramethylbutyl)phenol, 2,2'-methylenebis[4-t-butyl-6-(2H-benzotriazol-2-yl)phenol], a condensate of poly(3-11) (ethyleneglycol) with 2-[3'-t-butyl-2'-hydroxy-5'-(2-methoxycarbonylethyl)phenyl] benzotriazole, a condensate of poly(3-11) (ethyleneglycol) with methyl 3-[3-(2H-benzotriazol-2-yl)-5-t-butyl-4-hydroxyphenyl]propionate, 2-ethylhexyl 3-[3-t-butyl-5-(5-chloro-2H-benzotriazol-2-yl)-4-hydroxyphenyl]propionate, octyl 3-[3-t-butyl-5-(5-chloro-2H-benzotriazol-2-yl)-4-hydroxyphenyl]propionate, methyl 3-[3-t-butyl-5-(5-chloro-2H-benzotriazol-2-yl)-4-hydroxyphenyl]propionate, 3-[3-t-butyl-5-(5-chloro-2H-benzotriazol-2-yl)-4-hydroxyphenyl] propionic acid and any mixtures thereof.

As the light stabilizer, for example, the following can be mentioned. As the light stabilizer, the following compounds may be used alone or in combination of two or more.

(1) Examples of Hindered Amine Light Stabilizers

Bis(2,2,6,6-tetramethyl-4-piperidyl)sebacate, bis(2,2,6,6-tetramethyl-4-piperidyl)succinate, bis(1,2,2,6,6-pentamethyl-4-piperidyl)sebacate, bis(N-octoxy-2,2,6,6-tetramethyl-4-piperidyl)sebacate, bis(N-benzyloxy-2,2,6,6-tetramethyl-4-piperidyl)sebacate, bis(N-cyclohexyloxy-2,2,6,6-tetramethyl-4-piperidyl)sebacate, bis1,2,2,6,6-pentamethyl-4-piperidyl) 2-(3,5-di-t-butyl-4-hydroxybenzyl)-2-butylmalonate, bis(1-acroyl-2,2,6,6-tetramethyl-4-piperidyl) 2,2-bis(3,5-di-t-butyl-4-hydroxybenzyl)-2-butylmalonate, bis(1,2,2,6,6-pentamethyl-4-piperidyl)decanedioate, 2,2,6,6-tetramethyl-4-piperidyl methacrylate, 4-[3-(3,5-di-t-butyl-4-hydroxyphenyl)propionyloxy]-1-[2-(3-(3,5-di-t-butyl-4-hydroxyphenyl)propionyloxy)ethyl]-2,2,6,6-tetramethylpiperidine, 2-methyl-2-(2,2,6,6-tetramethyl-4-piperidyl)amino-N-(2,2,6,6-tetramethyl-4-piperidyl) propionamide, tetrakis(2,2,6,6-tetramethyl-4-piperidyl) 1,2,3,4-butanetetracarboxylate, tetrakis(1,2,2,6,6-pentamethyl-4-piperidyl) 1,2,3,4-butanetetracarboxylate, a mixed esterified product of 1,2,3,4-butanetetracarboxylic acid with 1,2,2,6,6-pentamethyl-4-piperidinol and 1-tridecanol, a mixed esterified product of 1,2,3,4-butanetetracarboxylic acid with 2,2,6,6-tetramethyl-4-piperidinol and 1-tridecanol, a mixed esterified product of 1,2,3,4-butanetetracarboxylic acid with 1,2,2,6,6-pentamethyl-4-piperidinol and 3,9-bis(2-hydroxy-1,1-dimethylethyl)-2,4,8,10-tetraoxaspiro [5.5]undecane, a mixed esterified product of 1,2,3,4-butanetetracarboxylic acid with 2,2,6,6-tetramethyl-4-piperidinol and 3,9-bis(2-hydroxy-1,1-dimethylethyl)-2,4,8,10-tetraoxaspiro[5.5]undecane, a polycondensate of dimethyl succinate with 1-(2-hydroxyethyl)-4-hydroxy-2,2,6,6-tetramethylpiperidine, poly[(6-morpholino-1,3,5-triazine-2,4-diyl)(2,2,6,6-tetramethyl-4-piperidyl)imino)hexamethylene ((2,2,6,6-tetramethyl-4-piperidyl)imino)], poly[(6-(1,1,3,3-tetramethylbutyl)imino-1,3,5-triazine-2,4-diyl((2,2,6,6-tetramethyl-4-piperidyl)imino)hexamethylene((2,2,6,6-tetramethyl-4-piperidyl)imino)], a polycondensate of N,N'-bis(2,2,6,6-tetramethyl-4-piperidyl)hexamethylenediamine with 1,2-dibromoethane, N,N',4,7-tetrakis[4,6-bis(N-butyl-N-(2,2,6,6-tetramethyl-4-piperidyl)amino)-1,3,5-triazine-2-yl]-4,7-diazadecane-1,10-diamine, N,N',4-tris[4,6-bis(N-butyl-N-(2,2,6,6-tetramethyl-4-piperidyl)amino)-1,3,5-triazin-2-yl]-4,7-diazadecane-1,10-diamine, N,N',4,7-tetrakis[4,6-bis(N-butyl-N-(1,2,2,6,6-pentamethyl-4-piperidyl)amino)-1,3,5-triazin-2-yl]-4,7-diazadecane-1,10-diamine, N,N',4-tris[4,6-bis(N-butyl-N-(1,2,2,6,6-pentamethyl-4-piperidyl)amino)-1,3,5-triazin-2-yl]-4,7-diazadecane-1,10-diamine and any mixtures thereof.

(2) Examples of Acrylate-Based Light Stabilizers

Ethyl α-cyano-β,β-diphenyl acrylate, isooctyl α-cyano-β,β-diphenyl acrylate, methyl α-carbomethoxycinnamate, methyl α-cyano-β-methyl-p-methoxycinnamate, butyl α-cyano-β-methyl-p-methoxycinnamate, methyl α-carbomethoxy-p-methoxycinnamate and N-(β-carbomethoxy-β-cyanovinyl)-2-methylindoline and any mixtures thereof.

(3) Examples of Nickel-Based Light Stabilizers

Nickel complexes of 2,2'-thiobis-[4-(1,1,3,3-tetramethylbutyl)phenol], nickeldibutyldithiocarbamate, nickel salts of monoalkyl esters, nickel complexes of ketoximes and any mixtures thereof.

(4) Examples of Oxamide-Based Light Stabilizers 4,4'-dioctyloxyoxanilide, 2,2'-diethoxyoxanilide, 2,2'-dioctyloxy-5,5'-di-t-butylanilide, 2,2'-didodecyloxy-5,5'-di-t-butylanilide, 2-ethoxy-2'-ethyloxanilide, N,N'-bis(3-dimethylaminopropyl)oxamide, 2-ethoxy-5-t-butyl-2'-ethoxyanilide, 2-ethoxy-5,4'-di-t-butyl-2'-ethyloxanilide and any mixtures thereof.

(5) Examples of 2-(2-Hydroxyphenyl)-1,3,5-Triazine Light Stabilizers 2,4,6-Tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-[2,4-dihydroxyphenyl-4,6-bis(2,4-dimethylphenyl]-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-[2-hydroxy-4-(2-hydroxy-3-butyloxypropoxy)phenyl]-4,6-bis(2,4-dimethylphenyl)-1,3,5-triazine, 2-[2-hydroxy-4-(2-hydroxy-3-octyloxypropoxy)phenyl]-4,6-bis(2,4-dimethylphenyl)-1,3,5-triazine and any mixtures thereof.

Examples of the metal deactivator include the followings.

N,N'-diphenyloxamide, N-salicylal-N'-salicyloylhydrazine, N,N'-bis(salicyloyl)hydrazine, N,N'-bis(3,5-di-t-butyl-4-hydroxyphenylpropionyl)hydrazine, 3-salicyloylamino-1,2,4-triazole, bis(benzylidene)oxalyldihydrazide, oxanilide, isophthaloyldihydrazide, sebacoylbisphenylhydrazide, N,N'-bis(salicyloyl)oxalyldihydrazide, N,N'-bis(salicyloyl)thiopropionyldihydrazide and any mixtures thereof.

Examples of the peroxide scavenger include esters of β-thiodipropionic acid, mercaptobenzimidazole, zinc salt of 2-mercaptobenzimidazole, zinc salt of dibutyldithiocarbamic acid, dioctadecyl disulfide, pentaerythritol tetrakis(R-dodecylmercapto)propionate, and any mixtures thereof.

Examples of the polyamide stabilizer include copper or divalent manganese salt of iodide or phosphorus compound, and any mixtures thereof.

Examples of the hydroxyamine include N,N-dibenzylhydroxyamine, N,N-diethylhydroxyamine, N,N-dioctylhydroxyamine, N,N-dilaurylhydroxyamine, N,N-ditetradecylhydroxylamine, N,N-dihexadecylhydroxyamine, N,N-dioctadecylhydroxyamine, N-hexadecyl-N-octadecylhydroxyamine, N-heptadecyl-N-octadecylhydroxyamine and any mixtures thereof.

Examples of the neutralizing agent include calcium stearate, zinc stearate, magnesium stearate, hydrotalcite (basic magnesium aluminum hydroxy carbonate hydrate), melamine, amine, polyamide, polyurethane, and any mixtures thereof.

Examples of the lubricant include aliphatic hydrocarbons such as paraffin and wax, higher fatty acids having 8 to 22 carbon atoms, higher fatty acid metal (Al, Ca, Mg, Zn) salts having 8 to 22 carbon atoms, aliphatic alcohols having 8 to 22 carbon atoms, polyglycols, esters of a higher fatty acid having 4 to 22 carbon atoms with an aliphatic monohydric alcohol having 4 to 18 carbon atoms, higher aliphatic amides having 8 to 22 carbon atoms, silicone oils, rosin derivatives.

Examples of the nucleating agent include the followings. Sodium 2,2'-methylenebis(4,6-di-t-butylphenyl)phosphate, [phosphate-2,2'-methylenebis(4,6-di-t-butylphenyl)]dihydroxyaluminum, bis[phosphate-2,2'-methylenebis(4,6-di-t-butylphenyl)]hydrooxyaluminum, tris[phosphate-2,2'-methylenebis(4,6-di-t-butylphenyl)]aluminum, sodium bis(4-t-butylphenyl)phosphate, metal salts of benzoic acid such as sodium benzoate, aluminum p-t-butylbenzoate, 1,3:2,4-bis(O-benzylidene)sorbitol, 1,3:2,4-bis(O-methylbenzylidene)sorbitol, 1,3:2,4-bis(O-ethylbenzylidene)sorbitol, 1,3-O-3,4-dimethylbenzylidene-2,4-O-benzylidene sorbitol, 1,3-O-benzylidene-2,4-O-3,4-dimethylbenzylidene sorbitol, 1,3:2,4-bis(O-3,4-dimethylbenzylidene)sorbitol, 1,3-O-p-chlorobenzylidene-2,4-O-3,4-dimethylbenzylidenesorbitol, 1,3-O-3,4-dimethylbenzylidene-2,4-O-p-chlorobenzylidenesorbitol, 1,3:2,4-bis(O-p-chlorobenzylidene)sorbitol and any mixtures thereof.

Examples of the filler include calcium carbonate, silicate, glass fiber, asbestos, talc, kaolin, mica, barium sulfate, carbon black, carbon fiber, zeolite, and any mixtures thereof.

Among these additives, preferred are phenolic antioxidants, phosphorus antioxidants, ultraviolet absorbers, hindered amine light stabilizers, peroxide scavengers and neutralizing agents.

Examples of particularly preferred phenolic antioxidant include the following compounds.

2,6-Di-t-butyl-4-methylphenol, 2,4,6-tri-t-butylphenol, 2,4-dioctylthiomethyl-6-methylphenol, 2,2'-thiobis(6-t-butylphenol), 4,4'-thiobis(3-methyl-6-t-butylphenol), 2,2'-methylenebis(4-methyl-6-t-butylphenol), 2,2'-methylenebis(4-ethyl-6-t-butylphenol), 2,2'-methylenebis[4-methyl-6-(α-methylcyclohexyl)phenol]], 2,2'-methylenebis(4-methyl-6-cyclohexylphenol), 2,2'-methylenebis(4,6-di-t-butylphenol), 2,2'-ethylidenebis(4,6-di-t-butylphenol), 4,4'-methylenebis(6-t-butyl-2-methylphenol), 4,4'-methylenebis(2,6-di-t-butylphenol), 4,4'-butylidenebis(3-methyl-6-t-butylphenol), 1,1-bis(4-hydroxyphenyl)cyclohexane, 1,1-bis(5-t-butyl-4-hydroxy-2-methylphenyl)butane, 1,1,3-tris(5-t-4-hydroxy-2-methylphenyl)butane, ethylene glycol bis[3,3-bis-3'-t-butyl-4'-hydroxyphenyl)butyrate], 2-t-butyl-6-(3'-t-butyl-5'-methyl-2'-hydroxybenzyl)-4-methylphenylacrylate, 2,4-di-t-pentyl-6-[1-2-hydroxy-3,5-di-t-pentylphenyl)ethyl]phenylacrylate, 2,4,6-tris(3,5-di-t-butyl-4-phenoxy)-1,3,5-triazine, tris(4-t-butyl-3-hydroxy-2,6-dimethylbenzyl)isocyanurate, bis(3,5-di-t-butyl-4-hydroxybenzyl)isocyanurate, tris[2-(3',5'-di-t-butyl-4'-hydroxycinnamoyloxy)ethyl]isocyanurate, diethyl-3,5-di-t-butyl-4-hydroxybenzylphosphonate, di-n-octadecyl-3,5-di-t-butyl-4-hydroxybenzylphosphonate, calcium salt of 3,5-di-t-butyl-4-hydroxybenzylphosphonic acid monoester, n-octadecyl 3-(3,5-di-t-butyl-4-hydroxyphenyl)propionate, neopentane tetrayltetrakis(3,5-di-t-butyl-4-hydroxycinnamate), thiodiethylenebis(3,5-di-t-butyl-4-hydroxycinnamate), 1,3,5-trimethyl-2,4,6-tris(3,5-di-t-butyl-4-hydroxybenzyl)benzene, 3,6-dioxaoctamethylenebis(3,5-di-t-butyl-4-hydroxycinnamate), hexamethylenebis(3,5-di-t-butyl-4-hydroxycinnamate), triethyleneglycolbis(5-t-butyl-4-hydroxy-3-methylcinnamate), 3,9-bis[2-(3-(3-t-butyl-4-hydroxy-5-methylphenyl)propionyloxy)-1,1-dimethylethyl]-2,4,4,10-tetraoxaspiro[5.5]undecane, N,N'-bis[3-(3',5'-di-t-butyl-4'-hydroxyphenyl)propionyl]hydrazine, N,N'-bis[3-(3',5'-di-t-butyl-4'-hydroxyphenyl)propionyl]hexamethylenediamine and the like.

Examples of particularly preferable phosphorus antioxidants include the following compounds.

Tris(nonylphenyl)phosphite, tris(2,4-di-t-butylphenyl)phosphite, distearylpentaerythritoldiphosphite, bis(2,4-di-t-butylphenyl)pentaerythritoldiphosphite, bis(2,4-di-t-butyl-6-methylphenyl)pentaerythritoldiphosphite, bis(2,6-di-t-butyl-4-methylphenyl)pentaerythritoldiphosphite, tetrakis(2,4-di-t-butylphenyl)-4,4'-diphenylenediphosphonite, 2,2'-methylenebis(4,6-di-t-butylphenyl) 2-ethylhexylphosphite, 2,2'-ethylidenebis(4,6-di-t-butylphenyl)fluorophosphite, bis(2,4-di-t-butyl-6-methylphenyl)ethylphosphite, 2-(2,4,6-tri-t-butylphenyl)-5-ethyl-5-butyl-1,3,2-oxaphosphorinane, 2,2',2"-nitrilo[triethyl-tris(3,3',5,5'-tetra-t-butyl-1,1'-biphenyl-2,2'-diyl)phosphite, 6-[3-(3-t-butyl-4-hydroxy-5-methylphenyl)propoxy]-2,4,8,10-tetra-t-butyldibenz[d,f][1,3,2]dioxaphosphepin and the like.

Examples of particularly preferred ultraviolet absorbers include the following compounds.

Phenyl salicylate, 4-t-butylphenylsalicylate, 2,4-di-t-butylphenyl 3',5'-di-t-butyl-4'-hydroxybenzoate, 4-t-octylphenylsalicylate, 2,4-dihydroxybenzophenone, 2-hydroxy-4- methoxybenzophenone, 2-hydroxy-4-octoxybenzophenone, 2,2'-dihydroxy-4-methoxybenzophenone, bis(5-benzoyl-4-hydroxy-2-methoxyphenyl)methane, 2,2',4,4'-tetrahydroxybenzophenone, 2-(2-hydroxy-5-methylphenyl)benzotriazole, 2-(3',5'-di-t-butyl-2'-hydroxyphenyl)benzotriazole, 2-(5'-t-butyl-2'-hydroxyphenyl)benzotriazole, 2-(2'-hydroxy-5'-t-octylphenyl)benzotriazole, 2-(3-t-butyl-2-hydroxy-5-methylphenyl)-5-chlorobenzotriazole, 2-(3'-S-butyl-2'-hydroxy-5'-t-butylphenyl)benzotriazole, 2-(2'-hydroxy-4'-octyloxyphenyl)benzotriazole, 2-(3',5'-di-t-amyl-2'-hydroxyphenyl)benzotriazole, 2-[2'-hydroxy-3',5'-bis(α,α-dimethylbenzyl)phenyl]-2H-benzotriazole and the like.

Examples of particularly preferable light stabilizers include the following compounds.

Bis(2,2,6,6-tetramethyl-4-piperidyl)sebacate, bis(1,2,2,6,6-pentamethyl-4-piperidyl)sebacate, bis(N-octoxy-2,2,6,6-tetramethyl-4-piperidyl)sebacate, bis(N-benzyloxy-2,2,6,6-tetramethyl-4-piperidyl)sebacate, bis(N-cyclohexyloxy-2,2,6,6-tetramethyl-4-piperidyl) sebacate, bis(1,2,2,6,6-pentamethyl-4-piperidyl) 2-(3,5-di-t-butyl-4-hydroxybenzyl)-2-butylmalonate, bis(1-acroyl-2,2,6,6-tetramethyl-4-piperidyl) 2,2-bis(3,5-di-t-butyl-4-hydroxybenzyl)-2-butylmalonate, bis(2,2,6,6-tetramethyl-4-piperidyl)succinate, 2,2,6,6-tetramethyl-4-piperidylmethacrylate, 4-[3-(3,5-di-t-butyl-4-hydroxyphenyl)propionyloxy]-1-[2-(3-(3,5-di-t-butyl-4-hydroxyphenyl)propionyloxy)ethyl]-2,2,6,6-tetramethylpiperidine, 2-methyl-2-(2,2,6,6-tetramethyl-4-piperidyl)amino-N-(2,2,6,6-tetramethyl-4-piperidyl) propionamide, tetrakis(2,2,6,6-tetramethyl-4-piperidyl) 1,2,3,4-butanetetracarboxylate, tetrakis(1,2,6,6-pentamethyl-4-piperidyl) 1,2,3,4-butanetetracarboxylate, a mixed esterified product of 1,2,3,4-butanetetracarboxylic acid with 1,2,2,6,6-pentamethyl-4-piperidinol and 1-tridecanol, a mixed esterified product of 1,2,3,4-butanetetracarboxylic acid with 2,2,6,6-tetramethyl-4-piperidinol and 1-tridecanol, a mixed esterified product of 1,2,3,4-butanetetracarboxylic acid with 1,2,2,6,6-pentamethyl-4-piperidinol and 3,9-bis(2-hydroxy-1,1-dimethylethyl)-2,4,8,10-tetraoxaspiro[5.5]undecane, a mixed esterified product of 1,2,3,4-butanetetracarboxylic acid with 2,2,6,6-tetramethyl-4-piperidinol and 3,9-bis(2-hydroxy-1,1-dimethylethyl)-2,4,8,10-tetraoxaspiro[5.5]undecane, a polycondensate of dimethyl succinate with 1-(2-hydroxyethyl)-4-hydroxy-2,2,6,6-tetramethylpiperidine, poly[(6-morpholino-1,3,5-triazine-2,4-diyl)((2,2,6,6-tetramethyl-4-piperidyl)imino)hexamethylene((2,2,6,6-tetramethyl-4-piperidyl)imino)], poly[(6-(1,1,3,3-tetramethylbutyl)-1,3,5-triazine-2,4-diyl)((2,2,6,6-tetramethyl-4-piperidyl)imino) hexamethylene((2,2,6,6-tetramethyl-4-piperidyl)imino)] and the like.

The phosphite compound of the present invention represented by the formula (I) and/or other additives which are added as required may be added to an organic material using any known method and apparatus for obtaining a homogeneous mixture. For example, when the organic material is a solid polymer, the phosphite compound of the present invention and/or other additives optionally added can be directly dry-blended with the solid polymer, or, it is also possible to add the phosphite compound and/or other additives optionally added to the solid polymer in the form of a masterbatch. When the organic material is a liquid polymer, in addition to the above-described addition method, the phosphite compound of the present invention and/or other additives optionally added may be added to the polymer solution during polymerization or immediately after polymerization, in the form of a solution or dispersion. On the other hand, when the organic material is a liquid (for example, oil) other than the solid polymer, in addition to the above-described addition method, the phosphite compound of the present invention and/or other additives optionally added may be added directly to the organic material for dissolution, or, the phosphite compound of the present invention and/or other additives optionally added may be added to a liquid medium in a dissolved or suspended state.

The phosphite compound of the present invention represented by the formula (I) has excellent performance as a stabilizer for various organic materials including thermoplastic resins such as polyolefins. The organic material to which the phosphite compound of the present invention is added is stable against thermal degradation, oxidation deterioration, etc. during production, processing, and further use, resulting in a high quality product.

EXAMPLES

Hereinafter, the present invention will be described in more detail by showing examples, but the present invention is not limited by these examples.
Measurement of $^1$H-NMR
 Apparatus: manufactured by bruker, AV-600 600 MHz
 Measurement solvent: $CDCl_3$
Measurement of MFR
 The measurement of MFR was carried out at 190° C. under a load of 2.16 kg using "Melt Indexer L 246-3537" manufactured by Technol Seven Co., Ltd.

Synthesis Example 1: Preparation of Compound 1A

Fifty g of ethyl acrylate, 200 ml of 1,4-dioxane as a solvent and 200 ml of distilled water were added under a nitrogen stream to a flask equipped with a thermometer, a stirrer and a cooling tube. 14.95 g of paraformaldehyde and 5.6 g of 1,4-diazabicyclo[2.2.2]octane were added, hydroquinone was further added as a polymerization inhibitor, and the mixture was stirred at room temperature for 6 days. Using an evaporator at 40° C., 1,4-dioxane as a reaction solvent was distilled off. Subsequently, the extraction operation, in which 100 ml of methyl t-butyl ether was added, and the mixture was shaken, followed by liquid separation, was performed three times. After washing the methyl t-butyl ether layer twice with 50 ml of water, methyl-t-butyl ether was distilled off using an evaporator to obtain 64.9 g of a crude product. The product was purified with a silica gel column using a mixed solvent of ethyl acetate and hexane (ethyl acetate:hexane=10:90 (volume ratio)) to obtain 35 g of Compound 1A. The yield was 43%. The same operation was repeated again to obtain the target product in a yield of 41.5%.

[Formula 8]

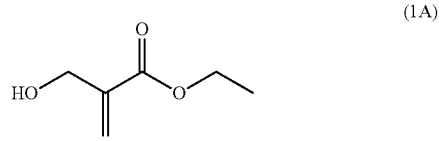

(1A)

Synthesis Example 2: Preparation of Compound 2A

One hundred fifty ml of diethyl ether and a catalytic amount of hydroquinone were added to a 500 ml flask containing 20.0 g of the compound 1A obtained in Synthesis Example 1 at room temperature. After cooling to 0 to −5° C., 5.2 g of PBr₃ was added dropwise. After completion of the dropwise addition, the ice bath was removed and the mixture was stirred at room temperature for 20 hours. 50 ml of ice water was added to the reaction mixture, and the mixture was washed three times with 50 ml of water. The obtained diethyl ether solution was dried by adding anhydrous sodium sulfate. Diethyl ether was distilled off from the solution using an evaporator at 35° C. to obtain 24 g of Compound 2A. The same operation was repeated again to obtain the target product in a yield of 70 to 80%.

[Formula 9]

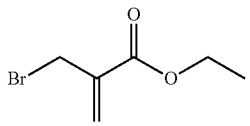

(2A)

Synthesis Example 3: Preparation of Compound 1B

Two hundred fifty ml of dichloromethane was added to a 1 L flask containing 25.0 g of 2-methyl-6-t-butylphenol at room temperature. After cooling to 0 to −5° C., 24.35 g of bromine was slowly added at room temperature, then the ice bath was removed and the mixture was stirred at room temperature for 10 hours. 187.5 ml of 1 M sodium sulfate was added at room temperature, the mixture was cooled to 0 to −5° C. and stirred for 30 minutes. The organic layer was washed with 250 ml of water and 250 ml of brine and then dried by adding anhydrous sodium sulfate. The obtained organic layer was concentrated with an evaporator to obtain 36 g of a crude product of Compound 1B. The yield was 98%. The same synthesis was carried out to obtain 145.0 g of the target product.

[Formula 10]

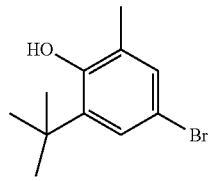

(1B)

Synthesis Example 4: Preparation of Compound 2B

To a 1 L flask containing 35.0 g of Compound 1B obtained in Synthesis Example 3, 350 ml of N,N-dimethylformamide was added at room temperature. 39.81 g of potassium carbonate was added at room temperature, the mixture was stirred for 15 minutes, and then cooled to 0 to −5° C. 40.46 g of methyl iodide was gradually added at room temperature, and after completion of the dropwise addition, the mixture was stirred at room temperature for 20 hours. 350 ml of ice water was added to the reaction mixture, which was stirred for 20 minutes, and extraction was carried out three times with 400 ml of ethyl acetate. The obtained organic layer was washed four times with 400 ml of water, washed with 400 ml of brine, and dried by adding anhydrous sodium sulfate. The organic layer was concentrated using an evaporator to obtain 36.9 g of a crude product. The product was purified with a silica gel column using a mixed solvent of ethyl acetate and hexane (ethyl acetate:hexane=5:95 (volume ratio)) to obtain 33.0 g of Compound 2B. The synthesis was repeated to obtain 121 g of Compound 2B in a yield of 78.1%.

[Formula 11]

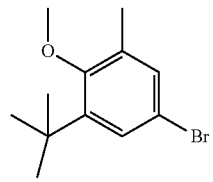

(2B)

Synthesis Example 5: Preparation of Compound 1C

Three point three g magnesium and a catalytic amount of iodine were added to a 500 ml flask. The mixture was heated from room temperature to 50° C. and stirred for 15 minutes. 30 ml of tetrahydrofuran (hereinafter referred to as THF) was added at room temperature, and then 5 ml of a solution prepared by dissolving 28.13 g of Compound 2A obtained in Synthesis Example 2 in 70 ml of THF was added. After the mixture was heated to 60° C. and stirred for 20 minutes, the remaining 65 ml was slowly added at room temperature and the resulting Grignard reagent was stirred at 60° C. for 2 hours and allowed to cool.

To a 500 ml flask, 19.2 g of Compound 2B obtained in Synthesis Example 4 and 95 ml of THF were added. After cooled to −78 to −80° C., the mixture was stirred for 20 minutes, and the Grignard reagent obtained above was dropped by syringe. After completion of the dropwise addition, the mixture was stirred at room temperature overnight. 100 ml of 10% hydrochloric acid was added, and the mixture was stirred at 0 to −5° C. for 20 minutes. THF was distilled off using an evaporator, and extraction was carried out three times with 350 ml of ethyl acetate. The organic layer was washed three times with 300 ml of water and once with 300 ml of brine and then dried by adding anhydrous sodium sulfate. The organic layer was concentrated with an evaporator to obtain 29.0 g of a crude product. The product was purified with a silica gel column using a mixed solvent of ethyl acetate and hexane (ethyl acetate:hexane=10:90 (volume ratio)) as a mobile phase to obtain 18.0 g of Compound 1C. The yield was 65%. Synthesis was performed again using 19.5 g of Compound 2A to obtain Compound 1C.

[Formula 12]

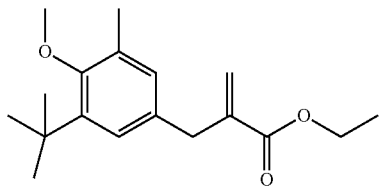

(1C)

Synthesis Example 6: Preparation of Compound 2C

Nineteen point five g of Compound 1C obtained in Synthesis Example 5 and 195 ml of dichloromethane were added to a 2 L flask, and the mixture was cooled to −78 to −80° C. and stirred for 30 minutes. Then, 343.78 ml of 25% diisobutylaluminum hydride-toluene solution was added dropwise. After completion of the dropwise addition, the mixture was stirred at room temperature overnight. After the completion of the reaction was confirmed, the mixture was cooled to 0 to −5° C. and 100 ml of a 10% water-methanol solution was added dropwise. 800 ml of dichloromethane was added at room temperature, and the mixture was stirred for 30 minutes. The solution was filtered and the residue was washed three times with 400 ml of warmed dichloromethane. The filtrate was concentrated with an evaporator to obtain 13.5 g of Compound 2C. The yield was 85%. The synthesis was repeated to obtain the target product in a yield of 75.7%.

[Formula 13]

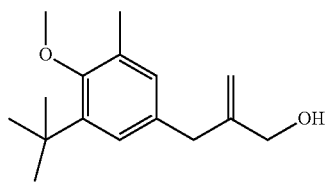

(2C)

Example 1: Production of Hydroxy Compound (2-t-butyl-4-(2-hydroxylmethyl-allyl)-6-methyl-phenol) of Formula (II-1)

Three g of Compound 2C obtained in Synthesis Example 6, 2 equivalents of ethyl sodium sulfide and 30 ml of N,N-dimethyl formamide were added to a 250 ml reactor capable of being capped, and the reactor was capped and heated at 140° C. in an oil bath for 2.5 hours. The reaction mixture was cooled to room temperature and diluted by adding 50 ml of ethyl acetate. The obtained organic layer was washed with 50 ml of a 10% hydrochloric acid aqueous solution, and the organic layer was separated. Subsequently, the organic layer was washed with 100 ml of brine, and N,N-dimethylformamide was completely removed. The organic layer was dried by adding anhydrous sodium sulfate and concentrated with an evaporator. The product was purified with a silica gel column using a mixed solvent of hexane and dichloromethane (hexane:dichloromethane=30:70 (volume ratio)) to obtain 0.94 g of the target product. The yield was 25%. The synthesis was repeated several times to obtain the target product in a yield of 20 to 25%.

[Formula 14]

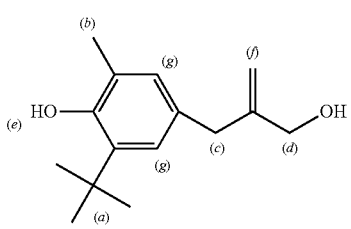

(II-1)

$^1$H-NMR (600 MHz, CDCl$_3$)
δ: 6.95 (d, 4J=2.4 Hz, 1H-g), 6.82 (d, 4J=2.4 Hz, 1H-g), 5.09, 4.90 (s, 2H-f), 4.67 (s, 1H-e), 4.05 (s, 2H-d), 3.30 (s, 2H-c), 2.22 (s, 3H-b), 1.40 (s, 9H-a)

Example 2: Production of Phosphite Compound Represented by Formula (I-1): 2-t-butyl-6-methyl-4-(2-{[(2,4,8,10-tetra-t-butyldibenzo[d,f][1,3,2]dioxaphosphepin-6-yl)oxy]methyl}prop-2-en-1-yl)phenol To a 500 ml flask containing 4.8 g of 2,2'-di-hydroxy-3,3',5,5'-tetra-t-butylbiphenyl and 48 ml of xylene was added 1.76 g of phosphorus trichloride at room temperature. After stirring the mixture at 50° C. for 30 minutes, 30 ml of N,N-diisopropylethylamine was slowly added dropwise at room temperature to the mixture, which was then heated to 55° C. and stirred at 55° C. for 1 hour. After cooling to room temperature, 30 ml of N,N-diisopropylethylamine was further added to the mixture, which was then stirred for 25 minutes. 3 g of the hydroxy compound obtained in Example 1 was dissolved in 48 ml of xylene and the solution was added dropwise to the 500 ml flask at a temperature of room temperature to 55° C. Then, the mixture was heated to 80° C. and stirred for 12 hours. After the completion of the reaction was confirmed by thin layer chromatography (ethyl acetate:hexane=5:95 as a mobile phase), the mixture was cooled to room temperature, 100 ml of ethyl acetate was added thereto, and the mixture was washed three times with 150 ml of water. The organic layer was separated and then dried by adding anhydrous sodium sulfate. The resultant organic layer was concentrated with an evaporator to obtain 8.1 g of a crude product. The crude product was purified with a silica gel column using a mixed solvent of ethyl acetate:hexane=5:95 (volume ratio) to obtain 5.2 g of white crystals. The yield was 69%. The synthesis was repeated several times to obtain the target product in a yield of 65 to 69%.

[Formula 15]

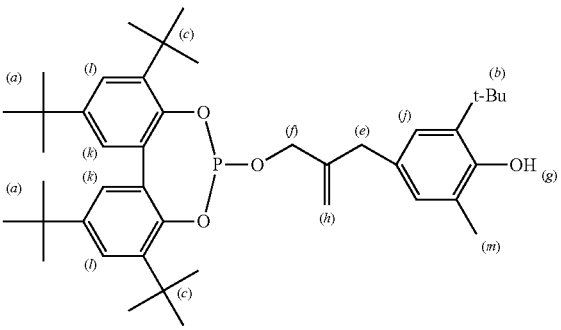

(I-1)

$^1$H-NMR (600 MHz, CDCl$_3$)
δ: 7.41 (d, 4J=2.3 Hz, 2H, Ar—H, (l)), 7.15 (d, 4J=2.3 Hz, 2H, Ar—H, (k)) 6.86 (d, 4J=2.3 Hz, 1H, Ar—H, (j)), 6.71 (d, 4J=2.3 Hz, 1H, Ar—H, (i)), 5.00, 4.82 (s, 2H, CH$_2$, (h)), 4.60 (s, 1H, OH, (g)), 4.13 (d, 3J=7.5 Hz, 2H, OCH$_2$, (f)), 3.19 (s, 2H, Ar—CH$_2$, (e)), 2.15 (s, 3H, Ar-Me, (m)), 1.46 (s, 18H, t-Bu, (c)), 1.35 (s, 27H, t-Bu, (a,b))

Example 3

Zero point one zero part by mass of the phosphite compound obtained in the same manner as in Example 2 and 0.05 part by mass of calcium stearate were added to 100 parts by mass of polyethylene (LLDPE) (GA 401 manufactured by Sumitomo Chemical Co., Ltd.), and the mixture was dry blended. Subsequently, the obtained blend was granulated at 190° C. using a single screw extruder to obtain pellets. Thereafter, the operation of placing the pellets again in a single screw extruder and extruding at 230° C. was repeated five times. The MFR value of the pellets was measured before (0 time) extrusion at 230° C. and after 1, 3, 5 extrusion operations. Table 1 shows MFR value after 5 extrusion operations and the ratio of MFR values between 0 and 5 times (5 times/0 time). Here, it is known that polyethylene degrades as crosslinking progresses by extrusion. This phenomenon can be observed as a decrease in MFR value. Therefore, the fact that the MFR value is maintained without decreasing even when the extrusion operation is repeated indicates that crosslinking of the polyethylene is suppressed and thus the processing stability of the polyethylene is high.

Comparative Example 1

The MFR of polyethylene was measured in the same manner as in Example 3 except that the phosphite compound represented by the formula (I-1) was not added to the polyethylene pellets. The obtained results are shown in Table 1.

Comparative Example 2

The MFR of polyethylene was measured in the same manner as in Example 3 except that 0.10 part by mass of 6-[3-(3-t-butyl-4-hydroxy-5-methylphenyl)propoxy]-2,4,8,10-tetra-t-butyldibenz[d,f][1,3,2]dioxaphosphepin, (Sumilizer® GP manufactured by Sumitomo Chemical Co., Ltd.) instead of the phosphite compound represented by the formula (I-1) was added to 100 parts by mass of polyethylene pellets. The obtained results are shown in Table 1.

TABLE 1

|  | MFR value [g/10 minutes] 5 times | Ratio of MFR values 5 times/0 time |
| --- | --- | --- |
| EXAMPLE 3 | 0.93 | 0.45 |
| COMPARATIVE EXAMPLE 1 | 0.33 | 0.22 |
| COMPARATIVE EXAMPLE 2 | 0.82 | 0.42 |

Example 4

Zero point one zero part by mass of the phosphite compound obtained in the same manner as in Example 2 and 0.05 part by mass of calcium stearate were added to 100 parts by mass of a powder of polypropylene (Homo-PP) (HS200, manufactured by Sumitomo Chemical Co., Ltd.), and the mixture was dry blended. Subsequently, the obtained blend was granulated at 230° C. using a single screw extruder to obtain pellets, and the MFR value was measured. Table 2 shows the MFR value. Here, it is known that polypropylene degrades due to extrusion and deteriorates. This phenomenon can be observed as an increase in MFR value. Therefore, the low MFR value indicates that polypropylene decomposition is suppressed and the processing stability of polypropylene is high.

Comparative Example 3

The MFR of polypropylene was measured in the same manner as in Example 4 except that the phosphite compound represented by the formula (I-1) was not added to the polypropylene powder. The obtained results are shown in Table 2.

TABLE 2

|  | MFR value |
| --- | --- |
| EXAMPLE 4 | 3.52 |
| COMPARATIVE EXAMPLE 3 | 9.66 |

The invention claimed is:

1. A phosphite compound represented by the formula (I)

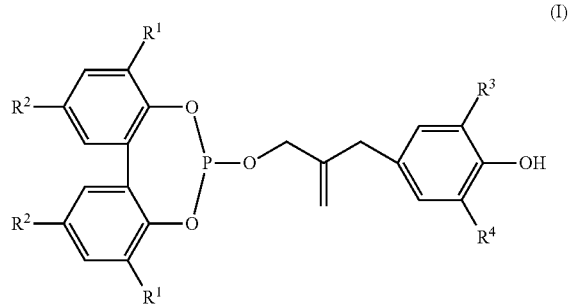

wherein $R^1$, $R^2$, $R^3$ and $R^4$ each independently represent a hydrogen atom, an alkyl group having 1 to 8 carbon atoms, a cycloalkyl group having 5 to 8 carbon atoms, an alkyl cycloalkyl group having 6 to 12 carbon atoms, an aralkyl group having 7 to 12 carbon atoms or an aryl group having 6 to 12 carbon atoms.

2. A hydroxy compound represented by the formula (II)

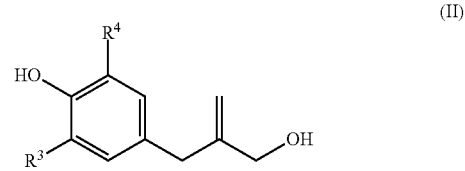

wherein $R^3$ and $R^4$ each independently represent a hydrogen atom, an alkyl group having 1 to 8 carbon atoms, a cycloalkyl group having 5 to 8 carbon atoms, an alkyl cycloalkyl group having 6 to 12 carbon atoms, an aralkyl group having 7 to 12 carbon atoms or an aryl group having 6 to 12 carbon atoms, provided that at least one of $R^3$ and $R^4$ is not hydrogen.

3. A method for producing the phosphite compound according to claim 1, wherein a hydroxy compound represented by formula (II)

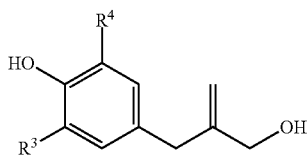

(II)

wherein R³ and R⁴ each independently represent a hydrogen atom, an alkyl group having 1 to 8 carbon atoms, a cycloalkyl group having 5 to 8 carbon atoms, an alkyl cycloalkyl group having 6 to 12 carbon atoms, an aralkyl group having 7 to 12 carbon atoms or an aryl group having 6 to 12 carbon atoms, a bisphenol compound represented by the formula (III)

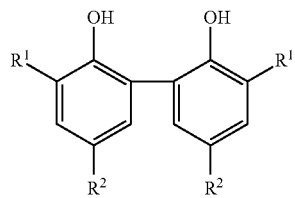

(III)

wherein $R^1$ and $R^2$ each independently represent a hydrogen atom, an alkyl group having 1 to 8 carbon atoms, a cycloalkyl group having 5 to 8 carbon atoms, an alkyl cycloalkyl group having 6 to 12 carbon atoms, an aralkyl group having 7 to 12 carbon atoms or an aryl group having 6 to 12 carbon atoms, and a phosphorus trihalide are reacted.

4. A stabilizer for an organic material, comprising the phosphite compound according to claim 1.

5. The stabilizer according to claim 4, wherein the organic material is a thermoplastic resin.

6. The stabilizer according to claim 5, wherein the thermoplastic resin is a polyolefin or an engineering plastic.

7. A method for stabilizing an organic material, wherein the phosphite compound according to claim 1 is added to an organic material.

8. The method according to claim 7, wherein the organic material is a thermoplastic resin.

9. The method according to claim 8, wherein the thermoplastic resin is a polyolefin or an engineering plastic.

10. A stabilized organic material composition comprising an organic material and a phosphite compound according to claim 1.

11. The composition according to claim 10, wherein the organic material is a thermoplastic resin.

12. The composition according to claim 11, wherein the thermoplastic resin is a polyolefin or an engineering plastic.

\* \* \* \* \*